United States Patent
Philippo et al.

(10) Patent No.: US 6,413,984 B1
(45) Date of Patent: Jul. 2, 2002

(54) 8-(HETEROCYCLYLMETHYL)QUINOLINE DERIVATIVES FOR TREATING URINARY INCONTINENCE

(75) Inventors: Christophe Philippo, Reuil Malmaison; Alain Braun, Boulogne Billancourt; Philippe R. Bovy, Mareil Marly, all of (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 09/890,526

(22) Filed: Aug. 1, 2001

(30) Foreign Application Priority Data

Feb. 2, 1999 (FR) .............................. 99 01145

(51) Int. Cl.[7] ................... A61K 31/47; A61K 31/4709; C07D 401/06
(52) U.S. Cl. ................... 514/314; 514/290; 514/297; 546/79; 546/93; 546/104; 546/176
(58) Field of Search ................... 546/79, 93, 104, 546/176; 514/290, 297, 314

(56) References Cited

PUBLICATIONS

Derwent Abstract 1998–325300.
Derwent Abstract 1998–437379.

Primary Examiner—Patricia L. Morris
(74) Attorney, Agent, or Firm—Paul E. Dupont; Michael D. Alexander

(57) ABSTRACT

The invention concerns compounds of formula (I) wherein: A represents either a hydrogen atom or a hydroxyl group; B represents a pyrrolidin-2-yl (D) or 2-piperidyl (E), B capable of being substituted by one or two $R_5$ groups; $R_1$ represents a hydrogen atom, a $C_1$–$C_6$ alkyl, a $C_2$–$C_6$ alkenyl, a $C_1$–$C_2$ perfluoroalkyl or a $C_1$–$C_6$ fluoroalkyl group; $R_2$, $R_3$ or $R_4$, independently of one another, represent a hydrogen atom, a $C_1$–$C_6$ alkyl, group or a $C_2$–$C_6$ alkenyl group, or $R_1$ and $R_2$ can together form a $C_1$–$C_6$ alkylene chain, or a $C_3$–$C_6$ alkenylene chain; $R_5$ represents a $C_1$–$C_6$ alkyl group, and $R_6$ represents a hydrogen atom, a $C_1$–$C_6$ alkyl group, a $C_2$–$C_6$ alkenyl group, $C_3$–$C_6$ cycloalkyl, $C_3$–$C_6$ cycloalkenyl or a benzyl. Said compounds have therapeutic applications

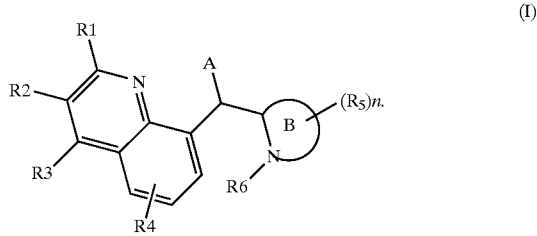

21 Claims, No Drawings

8-(HETEROCYCLYLMETHYL)QUINOLINE DERIVATIVES FOR TREATING URINARY INCONTINENCE

The present invention relates to α-azacyclomethylquinoline derivatives, to their preparation and to their therapeutic application.

The compounds correspond to the general formula (I):

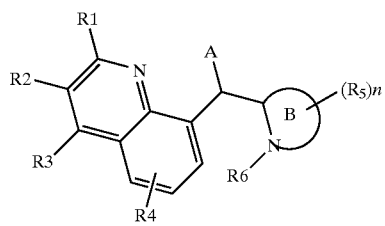

in which:
A represents either a hydrogen atom or a hydroxyl group,
B represents a 2-pyrrolidinyl (D) or 2-piperidyl (E),

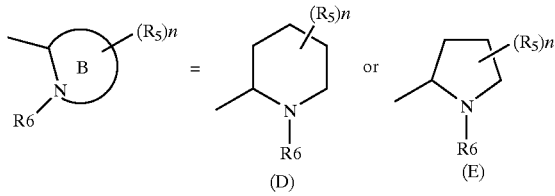

$R_1$ represents a hydrogen atom, a $C_{1-6}$ alkyl, $C_{2-6}$ alkenyl, $C_{1-2}$ perfluoroalkyl or $C_{1-6}$ fluoroalkyl group,
$R_2$, $R_3$ or $R_4$ represent, independently of each other, a hydrogen atom, a $C_{1-6}$ alkyl group or a $C_{2-6}$ alkenyl group, or
$R_1$ and $R_2$ together may also form a $C_{1-6}$ alkylene chain or a $C_{3-6}$ alkenylene chain,
$R_5$ represents a $C_{1-6}$ alkyl group,
$R_6$ represents a hydrogen atom, a $C_{1-6}$ alkyl group, a $C_{2-6}$ alkenyl group, a $C_{3-6}$ cycloalkyl group, a $C_{3-6}$ cycloalkenyl group or a benzyl, and
"n" represents 0, 1 or 2.

More particularly, the compounds for which A represents a hydroxyl group are preferred.

Moreover, the compounds for which $R_1$ represents a $C_{1-6}$ alkyl group, preferably $C_{1-3}$ alkyl and more particularly an ethyl, are found to be advantageous.

Other preferred compounds are the compounds for which $R_2$ and $R_3$ represent, independently of each other, a hydrogen atom or a $C_{1-3}$ alkyl group, more particularly a methyl.

The compounds for which A, $R_1$, $R_2$ and $R_3$ are as defined in the groups of preferred compounds are most particularly preferred.

In the context of the present invention, the term "$C_{1-6}$ alkyl" means a saturated, linear or branched aliphatic group comprising from 1 to 6 carbon atoms, such as, for example, a methyl, ethyl, propyl, isopropyl, butyl, isobutyl, tert-butyl, etc. group. The term "$C_{1-6}$ alkylene" denotes a divalent $C_{1-6}$ alkyl group.

The term "$C_{2-6}$ alkenyl" denotes a monounsaturated or polyunsaturated, linear or branched aliphatic group comprising from 2 to 6 carbon atoms. According to the invention, an alkenyl group preferably comprises 1 or 2 ethylenic unsaturations. The term "$C_{2-6}$ alkenylene" denotes a divalent $C_{2-6}$ alkenyl group.

The term "$C_{3-6}$ cycloalkyl" denotes a saturated cyclic aliphatic system comprising from 3 to 6 carbon atoms.

The term "$C_{3-6}$ cycloalkenyl" denotes a unsaturated cyclic aliphatic system comprising from 3 to 6 carbon atoms. According to the invention, a $C_{3-6}$ cycloalkenyl group preferably comprises 1 or 2 unsaturations.

The term "protecting group Pg" means a group which firstly protect a reactive function such as a hydroxyl or an amine during a synthesis, and secondly allows the reactive function to be regenerated intact at the end of the synthesis. Examples of protecting groups and protection and deprotection methods are given in *Protective group in Organic Synthesis Greene* et al., 2nd Ed. (John Wiley & Sons, Inc., New York).

Moreover, in the schemes, ● represents a solid support.

A solid support consists of an insoluble material bearing functionalization intended to capture a chemical compound.

Examples of such materials are polymers, plastics, resins, polysaccharides and silica derivatives. Preferably, resins are used, and more preferably polystyrene resins or resins of mixed polystyrene/ethylene glycol (PS-PEG) type.

Functionalization depends on the molecule to be captured. For example, this functionalization may consist of a halo, hydroxyl, aldehyde, carboxyl, amino, trityl or thiol group.

Such solid supports comprising suitable functionalization or which require a preactivation by methods known to those skilled in the art are commercially available in particular from Novabiochem, Rapp Polymer, Sigma, Aldrich, Polymer Laboratories or Argonaut Technologies.

Preferably, the solid support is a carboxy resin activated as acid chloride or a trityl chloride resin or an Elleman dihydropyran resin.

The compounds of general formula (I) may comprise one or more asymmetric carbon atoms. They may thus exist in the form of enantiomers or diastereoisomers. These enantiomers and diastereoisomers, and the mixtures thereof including racemic mixtures, form part of the invention.

The compounds of general formula (I) may be in the form of free base or of addition salts with acids, which also form part of the invention. According to the present invention, these salts comprise those with mineral or organic acids which allow a suitable separation or crystallization of the compounds of formula (I), such as picric acid, oxalic acid or an optically active acid, for example a tartaric acid, a dibenzoyltartaric acid, a mandelic acid or a camphorsulfonic acid, and those which form physiologically acceptable salts, such as the hydrochloride, hydrobromide, sulfate, hydrogen sulfate, dihydrogen phosphate, maleate, fumarate, citrate, pamoate, 2-naphthalenesulfonate or paratoluenesulfonate. Although the pharmaceutically acceptable salts are preferred, the other salts form part of the present invention. These salts may be prepared according to methods known to those skilled in the art, for example by reacting the compound of formula (I) in base form with the acid in a suitable solvent, such as an alcoholic solution or an organic solvent, followed by separation from the medium containing them by evaporation of the solvent or by filtration.

The compounds derived from α-azacyclomethylquinoline of formula (I) according to the invention may be prepared according to different processes. The compounds of formula (I), in particular those for which A represents a hydroxyl group, may be prepared according to the process described in Scheme 1.

According to this process, the compounds of formula (I) for which $R_6$ represents a hydrogen atom are obtained by cleaving from the solid support the compounds of formula (II) derived from the deprotection of the protecting group Pg on the nitrogen of the compound of formula (III), according to methods known to those skilled in the art. Such a protecting group may be, for example, a $C_{1-6}$ alkoxycarbonyl group such as tert-butyloxycarbonyl (tBoc). The meanings of $R_1$, $R_2$, $R_3$, $R_4$, $R_5$ and n in the compounds of formulae (II) and (III), are those given in formula (I).

The secondary amine in the compounds of formula (II) thus obtained may then be functionalized, according to processes known to those skilled in the art, for example by reductive amination (under the conditions described by Balasubranian et al., Tetrahedron Letters, vol. 37, No. 27, pp. 4819–4822) to give, after cleavage from the solid support, a compound of formula (I) in which $R_6$ is not a hydrogen.

The compounds of formula (III) may be obtained by uptake using an activated solid support of the reaction mixture derived from the reaction of an aldehyde of formula (VIII), in which Pg represents a protecting group known to those skilled in the art, with a derivative (IV) obtained by metallation of the halo derivative of formula (V). The meanings of $R_1$, $R_2$, $R_3$, $R_4$, $R_5$, B and n in the compounds of formulae (V) (IV) and (VIII) are those given in formula (I). The metallation reaction may be carried out in an organic solvent such as tetrahydrofuran, by forming the Grignard reagent of the halo derivative of formula (V), in which Y represents a halogen, or more advantageously by reacting the halo derivative of formula (V) in the presence of n-butyllithium preferably at temperatures of about −78° C. The term "metal" in formula (IV) represents, for example, lithium Li.

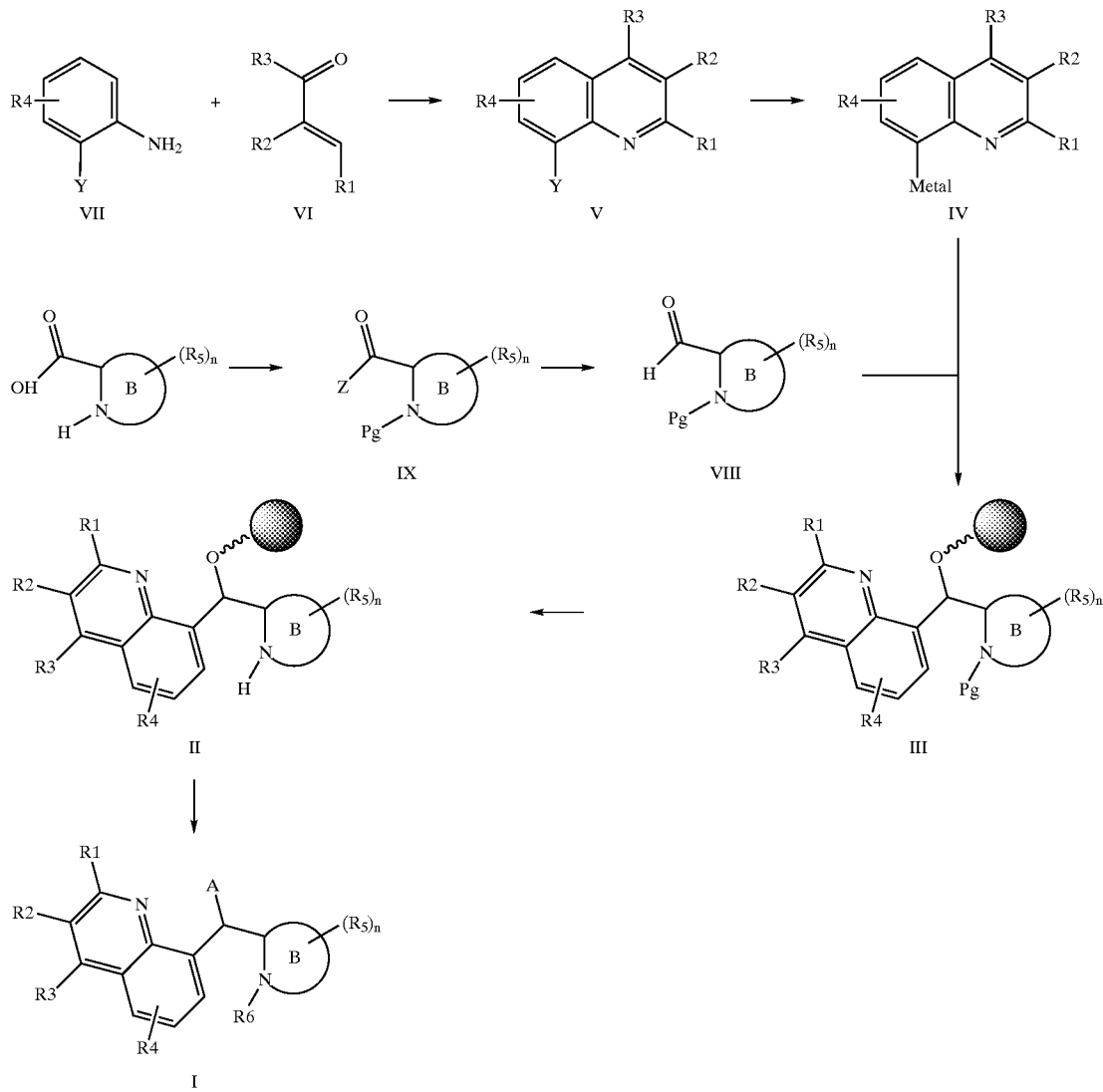

Scheme 1

The aldehydes of formula (VIII) may be obtained by reduction, for example according to the method described by Jurczack J. et al., Chem. Rev (1989), 89, 149, starting with the corresponding N-protected α-amino acid derivatives of formula (IX) which are themselves derived from the α-amino acids of formula (X). $R_5$, B and n have the meanings given in formula (I). Pg is defined as above and Z represents a group, which is known to those skilled in the art, allowing controlled reduction which stops at the formation of an aldehyde, inter alia, N-methyl-O- methylhydroxylamine (Nahm and Weinreb (1981), Tet., Lett., 22, 3815).

The compounds of formula (V) may themselves be prepared either by a Skraup or Doebner-Miller reaction. According to this process and under the conditions defined by Belser P. Tetrahedron 1996, Vol 52, No. 8, 2937–2944 or advantageously under the conditions defined by Z. Song J. Heterocyclic Chem. 1993, 30, 17–21, an aniline of formula (VII), for which Y represents a halogen such as a bromine or an iodine, and an α,β-unsaturated aldehyde or ketone of formula (VI) are heated in the presence of a dehydrating agent such as sulfuric acid and an oxidizing agent such as sodium iodide, to form a quinoline derivative substituted in position 8 with Y. The meanings of $R_1$, $R_2$, $R_3$ and $R_4$ in the compounds of formulae (V), (VI) and (VII) are those given in formula (I).

Alternatively, the compounds of formula (I) in which A represents a hydroxyl group may be prepared without using the resin, by keeping the hydroxyl group free.

The compounds of formula (I) according to the invention, for which A is a hydrogen atom, may be prepared by dehydroxylation of a corresponding compound of formula (I) in which A is a hydroxyl group.

The dehydroxylation reaction may be carried out, in a manner which is known to those skilled in the art, by reaction with triethylsilane and trifluoroacetic acid or according to the process described by Myers, A. G.; Movassaghi, M.; Zheng, B. J. Am. Chem. Soc. 1997, 119, 8572–8573.

The starting compounds, in particular those of formulae VII and VI, are commercially available or may be prepared according to methods known to those skilled in the art.

The examples which follow illustrate the processes and techniques suitable for preparing this invention, without, however, limiting the scope of the claim. The NMR and IR spectra, the mass spectra and the purity analyses by HPLC (purifications by liquid chromatography coupled to a mass detector) confirm the structures of the compounds.

Example 1

(R,R)-2-[2,3-dimethylquinol-8-yl)hydroxymethyl]-1-ethylpyrrolidine and (R,S)-2-[(2,3-dimethylquinol-8-yl)hydroxymethyl]-1-ethylpyrrolidine (1) 2,3-Dimethyl-8-bromoquinoline 55 ml of 70% sulfuric acid, 19 g (110.4 mmol) of 2-bromoaniline and 0.22 g (1.47 mmol) of sodium iodide are placed in a 500 ml three-necked flask fitted with a thermometer and a syringe plunger. The mixture is heated to 110° C. 2-Methyl-2-butenal (17 ml; 176 mmol) is added, at a rate of 4.23 ml/h, and stirring is continued for 40 min. The reaction mixture, cooled to room temperature, is poured onto crushed ice (2 l). The mixture obtained is made basic by adding sodium carbonate and is then extracted with dichloromethane (3×300 ml). The organic phases are combined, dried over magnesium sulfate and concentrated. The residue is purified by column chromatography on silica (elution solvent: 6:4 cyclohexane/ethyl acetate).

8.34 g (yield: 32%) of 2,3-dimethyl-8-bromoquinoline are obtained—m.p.: 78° C.

(2) 1,1-Dimethylethyl (R)-2-[(methoxymethylamino)carbonyl]pyrrolidine-1-carboxylate 13.0 g (56.8 mmol) of 1,1-dimethylethyl (R)-2-carboxypyrrolidine-1-carboxylate and 190 ml of dichloromethane are placed in a 500 ml three-necked flask fitted with a thermometer and a 250 ml addition funnel. The mixture is cooled to −20° C. on a bath of cardice and 7.91 ml (57 mmol) of triethylamine are added, followed by 7.01 ml (56.8 mmol) of pivaloyl chloride. The mixture is stirred vigorously for 15 minutes at −10° C., the temperature is then allowed to rise to 0° C., and a solution of 11.07 g (113 mmol) of N,O-dimethylhydroxylamine hydrochloride and 17.4 ml (125 mmol) of triethylamine in 160 ml of dichloromethane is added dropwise. The reaction mixture is allowed to warm to room temperature over 120 minutes and is then cooled to 0° C. on an ice bath and 100 ml of a 0.1N hydrochloric acid solution are added. The organic phase is washed successively with 100 ml of 0.2M sodium hydroxide solution and with 200 ml of brine, and is then dried over magnesium sulfate and concentrated. The residue is purified by chromatography on a column of silica (elution solvent: 50% ethyl acetate in cyclohexane). 14.26 g (yield: 92%) of 1,1-dimethylethyl (R)-2-[(methoxymethylamino)carbonyl] pyrrolidine-1-carboxylate are obtained in the form of a colorless oil.

(3) 1,1-Dimethylethyl (R)-2-formylpyrrolidine-1-carboxylate 0.80 g (21 mmol) of lithium aluminum hydride and 25 ml of ethyl ether are placed in a 125 ml round-bottomed flask. The suspension is cooled to −10° C. on an ice bath and a solution of 4.57 g (16.8 mmol) of 1,1-dimethylethyl(R)-2-[(methoxymethylamino)carbonyl]-pyrrolidone-1-carboxylate in 25 ml of ethyl ether is added dropwise. The reaction mixture is stirred for 45 minutes at −10° C., followed by addition of a solution of 3.43 g (25.2 mmol) of potassium bisulfate in 50 ml of water. The resulting mixture is extracted with ethyl acetate (3×80 ml). The organic phases are combined, washed with 120 ml of molar hydrochloric acid solution, 120 ml of saturated sodium bicarbonate solution, 120 ml of water and 120 ml of brine, dried over magnesium sulfate and concentrated. 3.03 g (yield: 84.5%) of 1,1-dimethylethyl (R)-2-formylpyrrolidine-1-carboxylate are obtained in the form of a colorless oil.

(4) Carboxylate Grafted onto a 1% divinylbenzene-polystyrene Resin of 1,1-dimethylethyl (R,R)-2-[(2, 3-dimethylquinol-8-yl)hydroxymethyl]pyrrolidine-1-carboxylate and 1,1-dimethylethyl (R,S) -2-[(2,3-dimethylquinol-8-yl)hydroxymethyl]pyrrolidine-1-carboxylate 0.7 g (3 mmol) of 2,3-dimethyl-8-bromoquinoline and 20 ml of anhydrous tetrahydrofuran are placed in a 100 ml three-necked flask. The solution is cooled to −78° C. on a bath of cardice in acetone, and 1.875 ml (3 mmol) of a 1.6M solution of n-butyllithium in hexane are added dropwise, followed by addition of a solution of 0.4 g (2 mmol) of 1,1-dimethylethyl (R)-2-formylpyrrolidine-1-carboxylate in 5 ml of anhydrous tetrahydrofuran. The reaction mixture is stirred for 75 minutes at −78° C. and 10 ml of water are then added dropwise. The resulting mixture is extracted with ethyl acetate (3×40 ml). The organic phases are combined, washed with 60 ml of water and 60 ml of brine, dried over magnesium sulfate and concentrated. The residue is placed in a thick-walled glass tube and 5 ml of dichloromethane, 0.50 g of carboxyl chloride grafted onto a 1% divinylbenzene-polystyrene resin (prepared according to the process described by Panek et al., Tetrahedron Letters, vol. 37, No. 45, 1996, pp. 8151–8154), 0.061 g of DMAP (dimethylaminopyridine) and 0.57 ml of triethylamine are added. The tube is sealed with a Teflon stopper and placed in an ultrasonic bath at 50° C. for 16 h. The resin is filtered off, rinsed with dichloromethane (10×10 ml) and dried under vacuum (550 mg obtained) to give the carboxylate grafted onto a 1% divinylbenzene-polystyrene resin of 1,1-dimethylethyl (R,R)-2-[(2,3-dimethylquinol-8-yl) hydroxymethyl)pyrrolidine-1-carboxylate and 1,1-dimethylethyl (R,S)-2-[(2,3-dimethylquinol-8-yl) hydroxymethyl]pyrrolidine-1-carboxylate.

An elemental analysis makes it possible to determine a nitrogen percentage of 3.15%, i.e. a resin containing 1.1 mmol/g.

(5) Carboxylate Grafted onto a 1% divinylbenzene-polystyrene Resin of (R,R)-2-[(2,3-dimethylquinol-8-yl)hydroxymethyl]pyrrolidine and (R,S)-2-[(2,3-dimethylquinol-8-yl)hydroxymethyl]pyrrolidine 0.10 g of carboxylate grafted onto a 1% divinylbenzene-polystyrene resin of 1,1-dimethylethyl (R,R)-2-[(2,3-dimethylquinol-8-yl)hydroxymethyl]pyrrolidine-1-carboxylate and 1,1-dimethylethyl (R,S)-2-[(2,3-dimethylquinol-8-yl)hydroxymethyl]pyrrolidine-1-carboxylate and 5 ml of a solution of trifluoroacetic acid (TFA) in dichloromethane (9/1) are placed in a PTFE flask. The suspension is stirred for 4 h at room temperature. The resin is filtered off, rinsed with dichloromethane (5×5 ml) and with a methanol/tetrahydrofuran (THF) solution (1/2) (5×5 ml) and then dried under vacuum to give the carboxylate grafted onto a 1% divinylbenzene-polystyrene resin of (R,R)-2-[(2,3-dimethylquinol-8-yl)hydroxymethyl] pyrrolidine and (R,S)-2-[(2,3-dimethylquinol-8-yl) hydroxymethyl]pyrrolidine.

(6) Carboxylate Grafted onto a 1% divinylbenzene-polystyrene Resin of (R,R)-2-[(2,3-dimethylquinol-8-yl)hydroxymethyl]-1-ethylpyrrolidine and (R,S)-2-[(2,3-dimethylquinol-8-yl)hydroxymethyl]-1-ethylpyrrolidine.

0.1 g of carboxylate grafted onto a 1% divinylbenzene-polystyrene resin of (R,R)-2-[(2,3-dimethylquinol-8-yl) hydroxymethyl]pyrrolidine and (R,S)-2-[(2,3-dimethylquinol-8-yl)hydroxymethyl]pyrrolidine, 5 ml of an ethanol/N,N-dimethylformamide (DMF) mixture (1/3), 0.4 mol of acetaldehyde and 0.4 ml of borane-pyridine (BAP) complex are placed in a tube. The mixture is stirred for 36 h at room temperature. The resin is filtered off, rinsed with an ethanol/DMF mixture (1/3) (3×5 ml), dichloromethane (2×5 ml), methanol (2×5 ml), dichloromethane (2×5 ml) and then dried under vacuum to give the carboxylate grafted onto a 1% divinylbenzene-polystyrene resin of (R,R)-2-[(2, 3-dimethylquinol-8-yl)hydroxymethyl]-1-ethylpyrrolidine and (R,S)-2-[(2,3-dimethylquinol-8-yl)hydroxymethyl]-1-ethylpyrrolidine (7) (R,R)-2-[(2,3-dimethylquinol-8-yl) hydroxymethyl]-1-ethylpyrrolidine and (R,S)-2-[(2, 3-dimethylquinol-8-yl)hydroxymethyl]-1-ethylpyrrolidine.

0.10 g of carboxylate grafted onto a 1% divinylbenzene-polystyrene resin of (R,R)-2-[(2,3-dimethylquinol-8-yl) hydroxymethyl]-1-ethylpyrrolidine and (R,S)-2-[(2,3-dimethylquinol-8-yl)hydroxymethyl]-1-ethylpyrrolidine, 5 ml of THF and 2.5 ml of tetrabutylammonium hydroxide as a molar solution in methanol are placed in a thick-walled glass tube. The tube is sealed with a Teflon stopper and placed in an ultrasonic bath at 50° C. for 16 h. The resin is filtered off and rinsed with a THF/methanol solution (2/1) (5×10 ml). The solution obtained from the washes is concentrated under vacuum and 15 ml of ethyl acetate are added. This solution is washed with water (3×10 ml), dried over magnesium sulfate and concentrated under vacuum to give a mixture of (R,R)-2-[(2,3-dimethylquinol-8-yl) hydroxymethyl]-1-ethylpyrrolidine and (R,S)-2-[(2,3-dimethylquinol-8-yl)hydroxymethyl]-1-ethylpyrrolidine.

EXAMPLE 2

2-Ethyl-3-methyl-8-bromoquinoline 240 ml of 70% sulfuric acid, 91.4 g (531 mmol) of 2-bromoaniline and 0.77 g (5.14 mmol) of sodium iodide are placed in a 1000 ml three-necked flask fitted with a thermometer and a syringe plunger. The mixture is heated to 170° C. 2-Methyl-2-pentenal (100 ml; 876 mmol) is added, at a rate of 25 ml/h, and stirring is continued for 1 h. The reaction mixture, cooled to room temperature, is poured onto crushed ice (2 l). The mixture obtained is made basic by adding sodium carbonate and the resulting mixture is then extracted with dichloromethane (3×300 ml). The organic phases are combined, dried over magnesium sulfate and concentrated. The residue is purified by column chromatography on silica (elution solvent: 6:4 cyclohexane/ethyl acetate) and then taken up in a small amount of pentane and slurried without heating. The precipitate obtained is filtered off and rinsed with a minimum amount of pentane.

11.2 g (yield: 8.4%) of 2-ethyl-3-methyl-8-bromoquinoline are obtained in the form of a white powder—m.p.: 54° C.

By repeating essentially the same process as in Example 1, with the appropriate starting materials, other compounds of formula (I) in accordance with the invention, listed in the table below, were prepared.

The table which follows collates the compounds of the invention and their physical characteristics.

TABLES

| In these tables: | 2HCl represents a dihydrochloride, nPr represents a linear propyl group, i-Pr represents an isopropyl group, Et represents an ethyl group, Me represents a methyl group, i-Bu represents an isobutyl group, Bn represents a benzyl group, |

TABLE 1

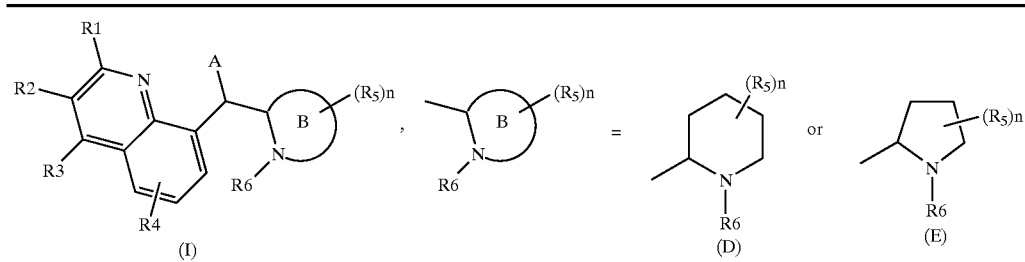

| No. | R₁ | R₂ | R₃ | R₄ | R₅ | R₆ | n | A | B | Salt | MS m/z (M⁺) |
|---|---|---|---|---|---|---|---|---|---|---|---|
| 1 | Me | H | H | H | — | H | 0 | OH | (E) (S) | 2HCl | 242 |
| 2 | Me | Me | H | H | — | H | 0 | OH | (E) (S) | 2HCl | 256 |
| 3 | Me | H | H | 6-Me | — | H | 0 | OH | (E) (S) | 2HCl | 256 |
| 4 | H | Me | Me | H | — | H | 0 | OH | (E) (S) | 2HCl | 256 |
| 5 | Et | H | H | H | — | H | 0 | OH | (E) (S) | 2HCl | 256 |
| 6 | n-Pr | H | H | H | — | H | 0 | OH | (E) (S) | 2HCl | 270 |
| 7 | Et | Me | H | H | — | H | 0 | OH | (E) (S) | 2HCl | 270 |
| 8 | Me | H | H | H | — | Me | 0 | OH | (E) (S) | 2HCl | 256 |
| 9 | Me | Me | H | H | — | Me | 0 | OH | (E) (S) | 2HCl | 270 |
| 10 | Me | H | H | 6-Me | — | Me | 0 | OH | (E) (S) | 2HCl | 270 |
| 11 | H | Me | Me | H | — | Me | 0 | OH | (E) (S) | 2HCl | 270 |
| 12 | Et | H | H | H | — | Me | 0 | OH | (E) (S) | 2HCl | 270 |
| 13 | n-Pr | H | H | H | — | Me | 0 | OH | (E) (S) | 2HCl | 284 |
| 14 | Et | Me | H | H | — | Me | 0 | OH | (E) (S) | 2HCl | 284 |
| 15 | Me | H | H | H | — | Et | 0 | OH | (E) (S) | 2HCl | 270 |
| 16 | Me | Me | H | H | — | Et | 0 | OH | (E) (S) | 2HCl | 284 |
| 17 | Me | H | H | 6-Me | — | Et | 0 | OH | (E) (S) | 2HCl | 284 |
| 18 | H | Me | Me | H | — | Et | 0 | OH | (E) (S) | 2HCl | 284 |
| 19 | Et | H | H | H | — | Et | 0 | OH | (E) (S) | 2HCl | 284 |
| 20 | n-Pr | H | H | H | — | Et | 0 | OH | (E) (S) | 2HCl | 298 |
| 21 | Et | Me | H | H | — | Et | 0 | OH | (E) (S) | 2HCl | 298 |
| 22 | Me | H | H | H | — | n-Pr | 0 | OH | (E) (S) | 2HCl | 284 |
| 23 | Me | Me | H | H | — | n-Pr | 0 | OH | (E) (S) | 2HCl | 298 |
| 24 | Me | H | H | 6-Me | — | n-Pr | 0 | OH | (E) (S) | 2HCl | 298 |
| 25 | H | Me | Me | H | — | n-Pr | 0 | OH | (E) (S) | 2HCl | 298 |
| 26 | Et | H | H | H | — | n-Pr | 0 | OH | (E) (S) | 2HCl | 298 |
| 27 | n-Pr | H | H | H | — | n-Pr | 0 | OH | (E) (S) | 2HCl | 312 |
| 28 | Et | Me | H | H | — | n-Pr | 0 | OH | (E) (S) | 2HCl | 312 |
| 29 | Me | H | H | H | — | i-Pr | 0 | OH | (E) (S) | 2HCl | 284 |
| 30 | Me | Me | H | H | — | i-Pr | 0 | OH | (E) (S) | 2HCl | 298 |
| 31 | Me | H | H | 6-Me | — | i-Pr | 0 | OH | (E) (S) | 2HCl | 298 |
| 32 | H | Me | Me | H | — | i-Pr | 0 | OH | (E) (S) | 2HCl | 298 |
| 33 | Et | H | H | H | — | i-Pr | 0 | OH | (E) (S) | 2HCl | 298 |
| 34 | n-Pr | H | H | H | — | i-Pr | 0 | OH | (E) (S) | 2HCl | 312 |
| 35 | Et | Me | H | H | — | i-Pr | 0 | OH | (E) (S) | 2HCl | 312 |
| 36 | Me | H | H | H | — | i-Bu | 0 | OH | (E) (S) | 2HCl | 298 |
| 37 | Me | Me | H | H | — | i-Bu | 0 | OH | (E) (S) | 2HCl | 312 |
| 38 | Me | H | H | 6-Me | — | i-Bu | 0 | OH | (E) (S) | 2HCl | 312 |
| 39 | H | Me | Me | H | — | i-Bu | 0 | OH | (E) (S) | 2HCl | 312 |
| 40 | Et | H | H | H | — | i-Bu | 0 | OH | (E) (S) | 2HCl | 312 |
| 41 | n-Pr | H | H | H | — | i-Bu | 0 | OH | (E) (S) | 2HCl | 326 |
| 42 | Et | Me | H | H | — | i-Bu | 0 | OH | (E) (S) | 2HCl | 326 |
| 43 | Me | H | H | H | — | c-Hex | 0 | OH | (E) (S) | 2HCl | 324 |
| 44 | Me | Me | H | H | — | c-Hex | 0 | OH | (E) (S) | 2HCl | 338 |
| 45 | Me | H | H | 6-Me | — | c-Hex | 0 | OH | (E) (S) | 2HCl | 338 |
| 46 | H | Me | Me | H | — | c-Hex | 0 | OH | (E) (S) | 2HCl | 338 |
| 47 | Et | H | H | H | — | c-Hex | 0 | OH | (E) (S) | 2HCl | 338 |
| 48 | n-Pr | H | H | H | — | c-Hex | 0 | OH | (E) (S) | 2HCl | 352 |
| 49 | Et | Me | H | H | — | c-Hex | 0 | OH | (E) (S) | 2HCl | 352 |
| 50 | Me | H | H | H | — | Bn | 0 | OH | (E) (S) | 2HCl | 332 |
| 51 | Me | Me | H | H | — | Bn | 0 | OH | (E) (S) | 2HCl | 346 |
| 52 | Me | H | H | 6-Me | — | Bn | 0 | OH | (E) (S) | 2HCl | 346 |
| 53 | H | Me | Me | H | — | Bn | 0 | OH | (E) (S) | 2HCl | 346 |
| 54 | Et | H | H | H | — | Bn | 0 | OH | (E) (S) | 2HCl | 346 |
| 55 | n-Pr | H | H | H | — | Bn | 0 | OH | (E) (S) | 2HCl | 360 |
| 56 | Et | Me | H | H | — | Bn | 0 | OH | (E) (S) | 2HCl | 360 |
| 57 | Me | H | H | H | — | H | 0 | OH | (D) (R) | 2HCl | 256 |
| 58 | Me | Me | H | H | — | H | 0 | OH | (D) (R) | 2HCl | 270 |
| 59 | Me | H | H | 6-Me | — | H | 0 | OH | (D) (R) | 2HCl | 270 |
| 60 | H | Me | Me | H | — | H | 0 | OH | (D) (R) | 2HCl | 270 |
| 61 | Et | H | H | H | — | H | 0 | OH | (D) (R) | 2HCl | 270 |
| 62 | n-Pr | H | H | H | — | H | 0 | OH | (D) (R) | 2HCl | 284 |
| 63 | Et | Me | H | H | — | H | 0 | OH | (D) (R) | 2HCl | 284 |

TABLE 1-continued

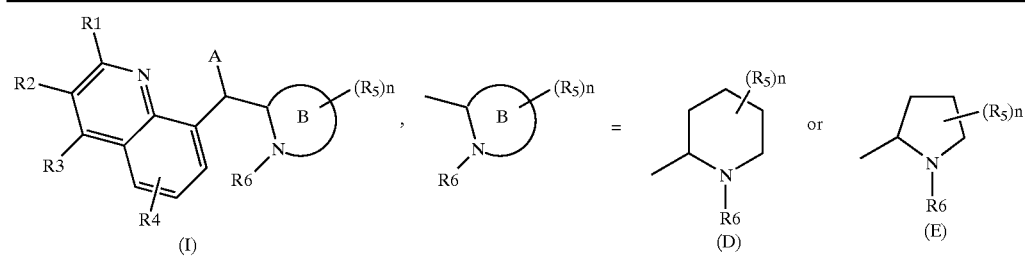

| No. | R₁ | R₂ | R₃ | R₄ | R₅ | R₆ | n | A | B | Salt | MS m/z (M⁺) |
|---|---|---|---|---|---|---|---|---|---|---|---|
| 64 | Me | H | H | H | — | Me | 0 | OH | (D) (R) | 2HCl | 270 |
| 65 | Me | Me | H | H | — | Me | 0 | OH | (D) (R) | 2HCl | 284 |
| 66 | Me | H | H | 6-Me | — | Me | 0 | OH | (D) (R) | 2HCl | 284 |
| 67 | H | Me | Me | H | — | Me | 0 | OH | (D) (R) | 2HCl | 284 |
| 68 | Et | H | H | H | — | Me | 0 | OH | (D) (R) | 2HCl | 284 |
| 69 | n-Pr | H | H | H | — | Me | 0 | OH | (D) (R) | 2HCl | 298 |
| 70 | Et | Me | H | H | — | Me | 0 | OH | (D) (R) | 2HCl | 298 |
| 71 | Me | H | H | H | — | Et | 0 | OH | (D) (R) | 2HCl | 284 |
| 72 | Me | Me | H | H | — | Et | 0 | OH | (D) (R) | 2HCl | 298 |
| 73 | Me | H | H | 6-Me | — | Et | 0 | OH | (D) (R) | 2HCl | 298 |
| 74 | H | Me | Me | H | — | Et | 0 | OH | (D) (R) | 2HCl | 298 |
| 75 | Et | H | H | H | — | Et | 0 | OH | (D) (R) | 2HCl | 298 |
| 76 | n-Pr | H | H | H | — | Et | 0 | OH | (D) (R) | 2HCl | 312 |
| 77 | Et | Me | H | H | — | Et | 0 | OH | (D) (R) | 2HCl | 312 |
| 78 | Me | H | H | H | — | n-Pr | 0 | OH | (D) (R) | 2HCl | 298 |
| 79 | Me | Me | H | H | — | n-Pr | 0 | OH | (D) (R) | 2HCl | 312 |
| 80 | Me | H | H | 6-Me | — | n-Pr | 0 | OH | (D) (R) | 2HCl | 312 |
| 81 | H | Me | Me | H | — | n-Pr | 0 | OH | (D) (R) | 2HCl | 312 |
| 82 | Et | H | H | H | — | n-Pr | 0 | OH | (D) (R) | 2HCl | 312 |
| 83 | n-Pr | H | H | H | — | n-Pr | 0 | OH | (D) (R) | 2HCl | 326 |
| 84 | Et | Me | H | H | — | n-Pr | 0 | OH | (D) (R) | 2HCl | 326 |
| 85 | Me | H | H | H | — | i-Pr | 0 | OH | (D) (R) | 2HCl | 298 |
| 86 | Me | Me | H | H | — | i-Pr | 0 | OH | (D) (R) | 2HCl | 312 |
| 87 | Me | H | H | 6-Me | — | i-Pr | 0 | OH | (D) (R) | 2HCl | 312 |
| 88 | H | Me | Me | H | — | i-Pr | 0 | OH | (D) (R) | 2HCl | 312 |
| 89 | Et | H | H | H | — | i-Pr | 0 | OH | (D) (R) | 2HCl | 312 |
| 90 | n-Pr | H | H | H | — | i-Pr | 0 | OH | (D) (R) | 2HCl | 326 |
| 91 | Et | Me | H | H | — | i-Pr | 0 | OH | (D) (R) | 2HCl | 326 |
| 92 | Me | H | H | H | — | i-Bu | 0 | OH | (D) (R) | 2HCl | 312 |
| 93 | Me | Me | H | H | — | i-Bu | 0 | OH | (D) (R) | 2HCl | 326 |
| 94 | Me | H | H | 6-Me | — | i-Bu | 0 | OH | (D) (R) | 2HCl | 326 |
| 95 | H | Me | Me | H | — | i-Bu | 0 | OH | (D) (R) | 2HCl | 326 |
| 96 | Et | H | H | H | — | i-Bu | 0 | OH | (D) (R) | 2HCl | 326 |
| 97 | n-Pr | H | H | H | — | i-Bu | 0 | OH | (D) (R) | 2HCl | 340 |
| 98 | Et | Me | H | H | — | i-Bu | 0 | OH | (D) (R) | 2HCl | 340 |
| 99 | Me | H | H | H | — | c-Hex | 0 | OH | (D) (R) | 2HCl | 338 |
| 100 | Me | Me | H | H | — | c-Hex | 0 | OH | (D) (R) | 2HCl | 352 |
| 101 | Me | H | H | 6-Me | — | c-Hex | 0 | OH | (D) (R) | 2HCl | 352 |
| 102 | H | Me | Me | H | — | c-Hex | 0 | OH | (D) (R) | 2HCl | 352 |
| 103 | Et | H | H | H | — | c-Hex | 0 | OH | (D) (R) | 2HCl | 352 |
| 104 | n-Pr | H | H | H | — | c-Hex | 0 | OH | (D) (R) | 2HCl | 366 |
| 105 | Et | Me | H | H | — | c-Hex | 0 | OH | (D) (R) | 2HCl | 366 |
| 106 | Me | H | H | H | — | Bn | 0 | OH | (D) (R) | 2HCl | 346 |
| 107 | Me | Me | H | H | — | Bn | 0 | OH | (D) (R) | 2HCl | 360 |
| 108 | Me | H | H | 6-Me | — | Bn | 0 | OH | (D) (R) | 2HCl | 360 |
| 109 | H | Me | Me | H | — | Bn | 0 | OH | (D) (R) | 2HCl | 360 |
| 110 | Et | H | H | H | — | Bn | 0 | OH | (D) (R) | 2HCl | 360 |
| 112 | n-Pr | H | H | H | — | Bn | 0 | OH | (D) (R) | 2HCl | 374 |
| 113 | Et | Me | H | H | — | Bn | 0 | OH | (D) (R) | 2HCl | 374 |
| 114 | Me | H | H | H | — | H | 0 | OH | (E) (R) | 2HCl | 242 |
| 115 | Me | Me | H | H | — | H | 0 | OH | (E) (R) | 2HCl | 256 |
| 116 | Me | H | H | 6-Me | — | H | 0 | OH | (E) (R) | 2HCl | 256 |
| 117 | H | Me | Me | H | — | H | 0 | OH | (E) (R) | 2HCl | 256 |
| 118 | Et | H | H | H | — | H | 0 | OH | (E) (R) | 2HCl | 256 |
| 119 | n-Pr | H | H | H | — | H | 0 | OH | (E) (R) | 2HCl | 270 |
| 120 | Et | Me | H | H | — | H | 0 | OH | (E) (R) | 2HCl | 270 |
| 121 | Me | H | H | H | — | Me | 0 | OH | (E) (R) | 2HCl | 256 |
| 122 | Me | Me | H | H | — | Me | 0 | OH | (E) (R) | 2HCl | 270 |
| 123 | Me | H | H | 6-Me | — | Me | 0 | OH | (E) (R) | 2HCl | 270 |
| 124 | H | Me | Me | H | — | Me | 0 | OH | (E) (R) | 2HCl | 270 |
| 125 | Et | H | H | H | — | Me | 0 | OH | (E) (R) | 2HCl | 270 |
| 126 | n-Pr | H | H | H | — | Me | 0 | OH | (E) (R) | 2HCl | 284 |
| 127 | Et | Me | H | H | — | Me | 0 | OH | (E) (R) | 2HCl | 284 |

TABLE 1-continued

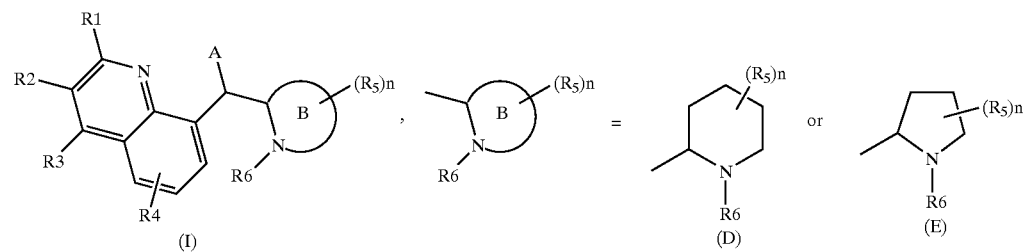

| No. | R₁ | R₂ | R₃ | R₄ | R₅ | R₆ | n | A | B | Salt | MS m/z (M⁺) |
|---|---|---|---|---|---|---|---|---|---|---|---|
| 128 | Me | H | H | H | — | Et | 0 | OH | (E) (R) | 2HCl | 270 |
| 129 | Me | Me | H | H | — | Et | 0 | OH | (E) (R) | 2HCl | 284 |
| 130 | Me | H | H | 6-Me | — | Et | 0 | OH | (E) (R) | 2HCl | 284 |
| 131 | H | Me | Me | H | — | Et | 0 | OH | (E) (R) | 2HCl | 284 |
| 132 | Et | H | H | H | — | Et | 0 | OH | (E) (R) | 2HCl | 284 |
| 133 | n-Pr | H | H | H | — | Et | 0 | OH | (E) (R) | 2HCl | 298 |
| 134 | Et | Me | H | H | — | Et | 0 | OH | (E) (R) | 2HCl | 298 |
| 135 | Me | H | H | H | — | n-Pr | 0 | OH | (E) (R) | 2HCl | 284 |
| 136 | Me | Me | H | H | — | n-Pr | 0 | OH | (E) (R) | 2HCl | 298 |
| 137 | Me | H | H | 6-Me | — | n-Pr | 0 | OH | (E) (R) | 2HCl | 298 |
| 138 | H | Me | Me | H | — | n-Pr | 0 | OH | (E) (R) | 2HCl | 298 |
| 139 | Et | H | H | H | — | n-Pr | 0 | OH | (E) (R) | 2HCl | 298 |
| 140 | n-Pr | H | H | H | — | n-Pr | 0 | OH | (E) (R) | 2HCl | 312 |
| 141 | Et | Me | H | H | — | n-Pr | 0 | OH | (E) (R) | 2HCl | 312 |
| 142 | Me | H | H | H | — | i-Pr | 0 | OH | (E) (R) | 2HCl | 284 |
| 143 | Me | Me | H | H | — | i-Pr | 0 | OH | (E) (R) | 2HCl | 298 |
| 144 | Me | H | H | 6-Me | — | i-Pr | 0 | OH | (E) (R) | 2HCl | 298 |
| 145 | H | Me | Me | H | — | i-Pr | 0 | OH | (E) (R) | 2HCl | 298 |
| 146 | Et | H | H | H | — | i-Pr | 0 | OH | (E) (R) | 2HCl | 298 |
| 147 | n-Pr | H | H | H | — | i-Pr | 0 | OH | (E) (R) | 2HCl | 312 |
| 148 | Et | Me | H | H | — | i-Pr | 0 | OH | (E) (R) | 2HCl | 312 |
| 149 | Me | H | H | H | — | i-Bu | 0 | OH | (E) (R) | 2HCl | 298 |
| 150 | Me | Me | H | H | — | i-Bu | 0 | OH | (E) (R) | 2HCl | 312 |
| 151 | Me | H | H | 6-Me | — | i-Bu | 0 | OH | (E) (R) | 2HCl | 312 |
| 152 | H | Me | Me | H | — | i-Bu | 0 | OH | (E) (R) | 2HCl | 312 |
| 153 | Et | H | H | H | — | i-Bu | 0 | OH | (E) (R) | 2HCl | 312 |
| 154 | n-Pr | H | H | H | — | i-Bu | 0 | OH | (E) (R) | 2HCl | 326 |
| 155 | Et | Me | H | H | — | i-Bu | 0 | OH | (E) (R) | 2HCl | 326 |
| 156 | Me | H | H | H | — | c-Hex | 0 | OH | (E) (R) | 2HCl | 324 |
| 157 | Me | Me | H | H | — | c-Hex | 0 | OH | (E) (R) | 2HCl | 338 |
| 158 | Me | H | H | 6-Me | — | c-Hex | 0 | OH | (E) (R) | 2HCl | 338 |
| 159 | H | Me | Me | H | — | c-Hex | 0 | OH | (E) (R) | 2HCl | 338 |
| 160 | Et | H | H | H | — | c-Hex | 0 | OH | (E) (R) | 2HCl | 338 |
| 161 | n-Pr | H | H | H | — | c-Hex | 0 | OH | (E) (R) | 2HCl | 352 |
| 162 | Et | Me | H | H | — | c-Hex | 0 | OH | (E) (R) | 2HCl | 352 |
| 163 | Me | H | H | H | — | Bn | 0 | OH | (E) (R) | 2HCl | 332 |
| 164 | Me | Me | H | H | — | Bn | 0 | OH | (E) (R) | 2HCl | 346 |
| 165 | Me | H | H | 6-Me | — | Bn | 0 | OH | (E) (R) | 2HCl | 346 |
| 166 | H | Me | Me | H | — | Bn | 0 | OH | (E) (R) | 2HCl | 346 |
| 167 | Et | H | H | H | — | Bn | 0 | OH | (E) (R) | 2HCl | 346 |
| 168 | n-Pr | H | H | H | — | Bn | 0 | OH | (E) (R) | 2HCl | 360 |
| 169 | Et | Me | H | H | — | Bn | 0 | OH | (E) (R) | 2HCl | 360 |
| 170 | Me | H | H | H | 4-Me (R) | H | 1 | OH | (D) (R) | 2HCl | 270 |
| 171 | Me | Me | H | H | 4-Me (R) | H | 1 | OH | (D) (R) | 2HCl | 285 |
| 172 | Me | H | H | 6-Me | 4-Me (R) | H | 1 | OH | (D) (R) | 2HCl | 285 |
| 173 | H | Me | Me | H | 4-Me (R) | H | 1 | OH | (D) (R) | 2HCl | 285 |
| 174 | Et | H | H | H | 4-Me (R) | H | 1 | OH | (D) (R) | 2HCl | 285 |
| 175 | n-Pr | H | H | H | 4-Me (R) | H | 1 | OH | (D) (R) | 2HCl | 299 |
| 176 | Et | Me | H | H | 4-Me (R) | H | 1 | OH | (D) (R) | 2HCl | 299 |
| 177 | Me | H | H | H | 4-Me (R) | Me | 1 | OH | (D) (R) | 2HCl | 285 |
| 178 | Me | Me | H | H | 4-Me (R) | Me | 1 | OH | (D) (R) | 2HCl | 299 |

TABLE 1-continued

| No. | R₁ | R₂ | R₃ | R₄ | R₅ | R₆ | n | A | B | Salt | MS m/z (M⁺) |
|---|---|---|---|---|---|---|---|---|---|---|---|
| 179 | Me | H | H | 6-Me | 4-Me (R) | Me | 1 | OH | (D) (R) | 2HCl | 299 |
| 180 | H | Me | Me | H | 4-Me (R) | Me | 1 | OH | (D) (R) | 2HCl | 299 |
| 181 | Et | H | H | H | 4-Me (R) | Me | 1 | OH | (D) (R) | 2HCl | 299 |
| 182 | n-Pr | H | H | H | 4-Me (R) | Me | 1 | OH | (D) (R) | 2HCl | 313 |
| 183 | Et | Me | H | H | 4-Me (R) | Me | 1 | OH | (D) (R) | 2HCl | 313 |
| 184 | Me | H | H | H | 4-Me (R) | Et | 1 | OH | (D) (R) | 2HCl | 299 |
| 185 | Me | Me | H | H | 4-Me (R) | Et | 1 | OH | (D) (R) | 2HCl | 313 |
| 186 | Me | H | H | 6-Me | 4-Me (R) | Et | 1 | OH | (D) (R) | 2HCl | 313 |
| 187 | H | Me | Me | H | 4-Me (R) | Et | 1 | OH | (D) (R) | 2HCl | 313 |
| 188 | Et | H | H | H | 4-Me (R) | Et | 1 | OH | (D) (R) | 2HCl | 313 |
| 189 | n-Pr | H | H | H | 4-Me (R) | Et | 1 | OH | (D) (R) | 2HCl | 327 |
| 190 | Et | Me | H | H | 4-Me (R) | Et | 1 | OH | (D) (R) | 2HCl | 327 |
| 191 | Me | H | H | H | 4-Me (R) | n-Pr | 1 | OH | (D) (R) | 2HCl | 312 |
| 192 | Me | Me | H | H | 4-Me (R) | n-Pr | 1 | OH | (D) (R) | 2HCl | 326 |
| 193 | Me | H | H | 6-Me | 4-Me (R) | n-Pr | 1 | OH | (D) (R) | 2HCl | 326 |
| 194 | H | Me | Me | H | 4-Me (R) | n-Pr | 1 | OH | (D) (R) | 2HCl | 326 |
| 195 | Et | H | H | H | 4-Me (R) | n-Pr | 1 | OH | (D) (R) | 2HCl | 326 |
| 196 | n-Pr | H | H | H | 4-Me (R) | n-Pr | 1 | OH | (D) (R) | 2HCl | 340 |
| 197 | Et | Me | H | H | 4-Me (R) | n-Pr | 1 | OH | (D) (R) | 2HCl | 340 |
| 198 | Me | H | H | H | 4-Me (R) | i-Pr | 1 | OH | (D) (R) | 2HCl | 312 |
| 199 | Me | Me | H | H | 4-Me (R) | i-Pr | 1 | OH | (D) (R) | 2HCl | 326 |
| 200 | Me | H | H | 6-Me | 4-Me (R) | i-Pr | 1 | OH | (D) (R) | 2HCl | 326 |
| 201 | H | Me | Me | H | 4-Me (R) | i-Pr | 1 | OH | (D) (R) | 2HCl | 326 |
| 202 | Et | H | H | H | 4-Me (R) | i-Pr | 1 | OH | (D) (R) | 2HCl | 326 |
| 203 | n-Pr | H | H | H | 4-Me (R) | i-Pr | 1 | OH | (D) (R) | 2HCl | 340 |
| 204 | Et | Me | H | H | 4-Me (R) | i-Pr | 1 | OH | (D) (R) | 2HCl | 340 |
| 205 | Me | H | H | H | 4-Me (R) | i-Bu | 1 | OH | (D) (R) | 2HCl | 326 |
| 206 | Me | Me | H | H | 4-Me (R) | i-Bu | 1 | OH | (D) (R) | 2HCl | 340 |
| 207 | Me | H | H | 6-Me | 4-Me (R) | i-Bu | 1 | OH | (D) (R) | 2HCl | 340 |
| 208 | H | Me | Me | H | 4-Me (R) | i-Bu | 1 | OH | (D) (R) | 2HCl | 340 |
| 209 | Et | H | H | H | 4-Me (R) | i-Bu | 1 | OH | (D) (R) | 2HCl | 340 |
| 210 | n-Pr | H | H | H | 4-Me (R) | i-Bu | 1 | OH | (D) (R) | 2HCl | 354 |
| 212 | Et | Me | H | H | 4-Me (R) | i-Bu | 1 | OH | (D) (R) | 2HCl | 354 |
| 213 | Me | H | H | H | 4-Me (R) | c-Hex | 1 | OH | (D) (R) | 2HCl | 352 |
| 214 | Me | Me | H | H | 4-Me (R) | c-Hex | 1 | OH | (D) (R) | 2HCl | 366 |
| 215 | Me | H | H | 6-Me | 4-Me (R) | c-Hex | 1 | OH | (D) (R) | 2HCl | 366 |
| 216 | H | Me | Me | H | 4-Me (R) | c-Hex | 1 | OH | (D) (R) | 2HCl | 366 |
| 217 | Et | H | H | H | 4-Me (R) | c-Hex | 1 | OH | (D) (R) | 2HCl | 366 |
| 218 | n-Pr | H | H | H | 4-Me (R) | c-Hex | 1 | OH | (D) (R) | 2HCl | 380 |
| 219 | Et | Me | H | H | 4-Me (R) | c-Hex | 1 | OH | (D) (R) | 2HCl | 380 |
| 220 | Me | H | H | H | 4-Me (R) | Bn | 1 | OH | (D) (R) | 2HCl | 360 |
| 221 | Me | Me | H | H | 4-Me (R) | Bn | 1 | OH | (D) (R) | 2HCl | 374 |
| 222 | Me | H | H | 6-Me | 4-Me (R) | Bn | 1 | OH | (D) (R) | 2HCl | 374 |
| 223 | H | Me | Me | H | 4-Me (R) | Bn | 1 | OH | (D) (R) | 2HCl | 374 |
| 224 | Et | H | H | H | 4-Me (R) | Bn | 1 | OH | (D) (R) | 2HCl | 374 |
| 225 | n-Pr | H | H | H | 4-Me (R) | Bn | 1 | OH | (D) (R) | 2HCl | 388 |
| 226 | Et | Me | H | H | 4-Me (R) | Bn | 1 | OH | (D) (R) | 2HCl | 388 |
| 227 | Me | H | H | H | 4-Me (R) | n-hex | 1 | OH | (D) (R) | 2HCl | 354 |
| 228 | Et | H | H | H | 4-Me (R) | n-hex | 1 | OH | (D) (R) | 2HCl | 368 |
| 229 | Et | Me | H | H | 4-Me (R) | n-hex | 1 | OH | (D) (R) | 2HCl | 383 |
| 230 | —(CH₂)₄— | | H | H | — | H | 0 | OH | (E) (S) | 2HCl | 282 |
| 231 | —(CH₂)₄— | | H | H | — | Me | 0 | OH | (E) (S) | 2HCl | 296 |
| 232 | —(CH₂)₄— | | H | H | — | Et | 0 | OH | (E) (S) | 2HCl | 310 |
| 233 | —(CH₂)₄— | | H | H | — | n-Pr | 0 | OH | (E) (S) | 2HCl | 324 |
| 234 | —(CH₂)₄— | | H | H | — | i-Pr | 0 | OH | (E) (S) | 2HCl | 324 |
| 235 | —(CH₂)₄— | | H | H | — | Bn | 0 | OH | (E) (S) | 2HCl | 372 |

All the compounds in this table are pairs of diastereoisomers: stereochemistry of the carbon bearing the group A (OH) is not defined, the stereochemistry of the carbon bearing the nitrogen is specified in the column relating to the nitrogenous ring (B).

mixture of 95% $O_2$ and 5% $CO_2$ maintained at 37° C. The blood vessel is linked to an isometric sensor under a basal tension of 1 g and is connected to a polygraph for recording the variations in tension. The viability of each preparation is tested by pre-stimulation with 3 µM noradrenalin. After

TABLE 2

| No. | $R_1$ | $R_2$ | $R_3$ | $R_4$ | $R_5$ | n | $R_6$ | B | A | Salt | PF (° C.) |
|-----|-------|-------|-------|-------|-------|---|-------|-----|-------|---------|-----|
| 236 | Me | Me | H | H | — | 0 | H | (E) (R) | OH (S) | 2HCl | 215 |
| 237 | Me | Me | H | H | — | 0 | Et | (E) (R) | OH (S) | citrate | 90 |
| 238* | Me | Me | H | H | — | 0 | Et | (E) (R) | OH (S) | 2HCl | 55 |
| 239 | Et | Me | H | H | — | 0 | Et | (E) (R) | OH (S) | 2HCl | 165 |
| 240 | Et | Me | H | H | — | 0 | Et | (E) (R) | OH (R) | pamoate | 113 |

In this table, the stereochemistry of the carbon bearing the group A (OH) is specified in the column relating to the group A, the stereochemistry of the carbon bearing nitrogen (N) is specified in the column relating to the nitrogenous ring (B). The compounds whose number is accompanied by an "*" are in the form of a pair of diastereoisomers. All the other compounds in this table are chiral.

The compounds of the invention were subjected to biological tests intended to demonstrate their contractile activity on urethral and arterial smooth muscles.

1. The in vitro activity of the compounds of the invention was studied on urethral and arterial smooth muscles. These tests were carried out on female new Zealand rabbits weighing from 3 to 3.5 kg. The animals were killed by vertebral dislocation, and rings of urethral and mesenteric artery tissue were then taken. These rings of tissue were immersed in a modified Krebs solution, oxygenated with a mixture of 95% $O_2$ and 5% $CO_2$. Each sample of tissue was subjected to a tension of 1 g, after which phenylephrine was introduced at cumulative doses and the dose/response curve was established. After rinsing the samples, the compound to be studied was introduced at cumulative doses and the dose/response curve was established. The contractile effect of each compound is evaluated by calculating the $pD_2$ (negative logarithm of the agonist concentration which induces 50% of the maximum contraction) as well as by the maximum effect representing the percentage of the maximum contraction obtained with phenylephrine (% $E_{max}$).

The results obtained show that the compounds in accordance with the invention have:
- a urethral $pD_2$ usually of between 4 and 8,
- an arterial $pD_2$ usually of less than 3,
- a urethral % $E_{max}$ of greater than 30, usually between 40 et 90,
- an arterial % $E_{max}$ usually equal to zero.

2. The in vitro activity of the compounds of the invention were studied on the saphene veins of Yucatan miniature pig. The tissue is cut into a spiral and is mounted in an isolated organ tank in a modified Krebs solution oxygenated with a rinsing, the test compound is introduced and its concentration-response curve is constructed cumulatively until a maximum response is obtained. The contractile effect of each compound is evaluated by calculating the $EC_{50}$ (concentration producing 50% of the maximum response).

The compounds of the invention made it possible to obtain vasoconstrictive activity with an $EC_{50}$ value usually of between 1 µM et 100 µM.

The compounds of the invention may be used in the treatment of venous insufficiency and venous ulcers.

3. The in vivo activity of the compounds of the invention on urethral and blood pressure were studied in demyelinized rats and in rabbits, according to the following protocols:

Pithed Rats

Wistar rats are anesthetized and pithed (according to the technique described by Gillespie, MacLaren A. and Polock D., A method of stimulating different segments of the autonomic outflow from the spinal column to various organs in the pithed cat and rat; Br. J. Pharmacol., 1970, 40: 257–267).

Catheters are introduced via the aorta and a jugular vein. Another catheter is introduced into the urethra via an incision made in the bladder. The test compounds are administered at increasing doses by intravenous perfusion.

The results are expressed as doses (µg/kg) required to increase the urethral pressure by 10 cm of water ($UP_{10}$) or the arterial pressure by 10 mmHg ($AP_{10}$), i.e. 10/760 atm, or 50 mmHg ($AP_{50}$), i.e. 50/760 atm.

The compounds of the invention thus tested made it possible to obtain:
- a $UP_{10}$ with doses of less than 500 µg/kg, usually between 50 and 200 µg/kg,
- an $AP_{10}$ with doses of greater than 600 µg/kg, usually between 600 and 2000 µg/kg,
- the $AP_{50}$ could not be reached.

The above set of results show that the compounds of the invention have strong urethral contractile action and weak arterial contractile action.

They may be used as medicinal products, in particular as agents for contracting smooth muscles, and even more particularly in the treatment of urinary exertion incontinence. In this indication, the compounds according to the invention show good efficacy and, usually, lower side effects than the medicinal products conventionally used for such a treatment, in particular as regards the side effects affecting the cardiovascular system, in particular the arterial beds.

The compounds according to the invention can also be used for the treatment of veinous insufficiency, migraine, gastrointestinal disorders and as vasoconstrictors of nasal mucosa.

The use of the compounds according to the invention for the preparation of a medicinal product intended for treating the pathologies mentioned above forms an integral part of the invention.

According to another of its aspects, the present invention relates to pharmaceutical compositions containing a compound according to the invention as active principle.

Thus, these pharmaceutical compositions contain an effective dose of a compound according to the invention or of a pharmaceutically acceptable salt or hydrate thereof, and one or more pharmaceutically acceptable excipients.

The said excipients are chosen according to the desired pharmaceutical form and the desired mode of administration.

In the pharmaceutical compositions of the present invention for oral, sublingual, subcutaneous, intramuscular, intravenous, topical, intratracheal, intranasal, transdermal or rectal administration, the active principle of formula (I) above or its possible salt or hydrate can be administered in unit administration form, mixed with conventional pharmaceutical excipients, to animals and human beings for the prophylaxis or treatment of the above disorders or diseases. The appropriate unit administration forms comprise oral-route forms such as tablets, gel capsules, powders, granules and oral solutions or suspensions, sublingual, buccal, intratracheal and intranasal administration forms, subcutaneous, intramuscular or intravenous administration forms and rectal administration forms. The compounds according to the invention can be used in creams, ointments or lotions for topical application.

In order to obtain the desired prophylactic or therapeutic effect, the dose of active principle can vary between 0.1 mg et 50 mg per kg of body weight and per day. Although these dosages are examples of an average situation, there may be particular cases in which higher or lower dosages are appropriate, and such dosages also form part of the invention. According to the usual practice, the dosage which is appropriate for each patient is determined by the doctor according to the mode of administration and the weight and response of said patient.

Each unit dose can contain from 0.1 to 1000 mg, preferably from 1 to 500 mg, of active principle combined with a pharmaceutical excipient. This unit dose can be administered 1 to 5 times a day so as to administer a daily dosage of from 0.5 to 5000 mg, preferably from 1 to 2500 mg.

For example, when a solid composition in the form of tablets is prepared, the main active ingredient is mixed with a pharmaceutical excipient, such as gelatin, starch, lactose, magnesium stearate, talc, gum arabic or the like. The tablets can be coated with sucrose, a cellulose derivative or other materials. The tablets can be made via different techniques: direct tabletting, dry granulation, wet granulation or hot melting.

According to a second example, a preparation as gel capsules is obtained by mixing the active ingredient with a diluent and pouring the mixture obtained into soft or hard gel capsules.

Aqueous suspensions, isotonic saline solutions or sterile, injectable solutions which contain pharmacologically compatible dispersants and/or wetting agents, for example propylene glycol or butylene glycol, are used for parenteral administration.

According to another of its aspects, the present invention also relates to a method for treating the pathologies indicated above, which comprises the administration of a compound according to the invention or a salt or hydrate thereof.

What is claimed is:

1. A compound of formula (I)

(I)

[chemical structure showing quinoline with substituents R1, R2, R3, R4 on the ring system, group A connecting to group B with (R5)n and R6]

in which:

A represents either a hydrogen atom or a hydroxyl group,

B represents a 2-pyrrolidinyl (D) or 2-piperidyl (E),

[chemical structures showing B group (D) piperidyl and (E) pyrrolidinyl with R6 and (R5)n]

$R_1$ represents a hydrogen atom, a $C_{1-6}$ alkyl, $C_{2-6}$ alkenyl, $C_{1-2}$ perfluoroalkyl or $C_{1-6}$ fluoroalkyl group, $R_2$, $R_3$ or $R_4$ represent, independently of each other, a hydrogen atom, a $C_{1-6}$ alkyl group or a $C_{2-6}$ alkenyl group, or $R_1$ and $R_2$ together may also form a $C_{1-6}$ alkylene chain or a $C_{3-6}$ alkenylene chain, $R_5$ represents a $C_{1-6}$ alkyl group, $R_6$ represents a hydrogen atom, a $C_{1-6}$ alkyl group, a $C_{2-6}$ alkenyl group, a $C_{3-6}$ cycloalkyl group, a $C_{3-6}$ cycloalkenyl group or a benzyl, and "n" represents 0, 1 or 2, or a salt thereof.

2. A compound according to claim 1 wherein A represents a hydroxyl group.

3. A compound according to claim 1 wherein $R_1$ represents $C_{1-3}$ alkyl.

4. A compound according to claim 1 wherein $R_2$ and $R_3$ represent, independently of each other, a hydrogen atom or a $C_{1-3}$ alkyl group.

5. A process for preparing a compound according to claim 1 which comprises reacting an aldehyde of formula (VIII)

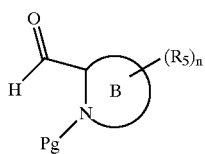

with an organometallic quinoline derivative of formula (IV)

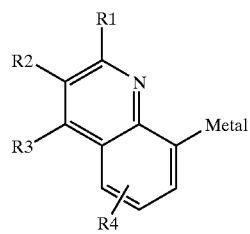

in which the meanings of $R_1$, $R_2$, $R_3$, $R_4$, $R_5$, B and n in the aldehyde of formula (VIII) and in the quinoline derivative of formula (IV) are as defined in claim 1 and Pg represents a protecting group, followed by a deprotection of the amine, to give a compound according to claim 1 in which A represents a hydroxyl and $R_6$ represents a hydrogen, and optionally by a functionalization of the amine to give a compound according to claim 1, in which $R_6$ is other than a hydrogen, and optionally followed by a dehydroxylation to give a compound according to claim 1 in which A is a hydrogen.

6. A pharmaceutical composition comprising a compound according to claim 1 and one or more suitable excipients.

7. A compound according to claim 2 wherein $R_1$ is $C_{1-3}$ alkyl.

8. A compound according to claim 2 wherein $R_2$ and $R_3$ are independently hydrogen or $C_{1-3}$ alkyl.

9. A compound according to claim 3 wherein $R_2$ and $R_3$ are independently hydrogen or $C_{1-3}$ alkyl.

10. A compound according to claim 9 selected from the group consisting of (R,R)-2-[(2,3-dimethylquinol-8-yl)hydroxymethyl]-1-ethylpyrrolidine and (R,S)-2-[(2,3-dimethylquinol-8-yl)hydroxymethyl]-1-ethylpyrrolidine.

11. A pharmaceutical composition comprising a compound according to claim 2 and one or more suitable excipients.

12. A pharmaceutical composition comprising a compound according to claim 3 and one or more suitable excipients.

13. A pharmaceutical composition comprising a compound according to claim 4 and one or more suitable excipients.

14. A pharmaceutical composition comprising a compound according to claim 10 and one or more suitable excipients.

15. A method for treating urinary incontinence, veinous insufficiency, migraine or gastrointestinal disorders, or for effecting vasoconstriction of the nasal mucosa which comprises administering to a patient in need thereof a therapeutically effective amount of a compound according to claim 1.

16. A method according to claim 15 for the treatment of urinary incontinence.

17. A method according to claim 16 for the treatment of urinary exertion incontinence.

18. A method for the treatment of urinary exertion incontinence which comprises administering to a patient in need of such treatment a therapeutically effective amount of a compound according to claim 2.

19. A method for the treatment of urinary exertion incontinence which comprises administering to a patient in need of such treatment a therapeutically effective amount of a compound according to claim 3.

20. A method for the treatment of urinary exertion incontinence which comprises administering to a patient in need of such treatment a therapeutically effective amount of a compound according to claim 4.

21. A method for the treatment of urinary exertion incontinence which comprises administering to a patient in need of such treatment a therapeutically effective amount of a compound according to claim 10.

* * * * *